US006451761B1

(12) United States Patent
van Gelder et al.

(10) Patent No.: US 6,451,761 B1
(45) Date of Patent: Sep. 17, 2002

(54) N'N'-DICHLORINATED OMEGA-AMINO ACIDS AND USES THEREOF

(75) Inventors: Nico M. van Gelder, Yarker (CA); Raymond J. Bowers, Bath (CA)

(73) Assignee: Queen's University at Kingston, Kingston (CA)

( * ) Notice: Subject to any disclaimer, the term of this patent is extended or adjusted under 35 U.S.C. 154(b) by 39 days.

(21) Appl. No.: 09/670,022

(22) Filed: Sep. 26, 2000

Related U.S. Application Data

(60) Provisional application No. 60/156,528, filed on Sep. 29, 1999.

(51) Int. Cl.[7] .................. A61K 31/197; A61K 31/20; A61K 31/662; A61K 38/02; C07K 2/00
(52) U.S. Cl. ..................... 514/2; 514/114; 514/558; 514/561; 514/578; 530/300; 554/103; 554/114; 562/11; 562/104
(58) Field of Search ................. 514/2, 114, 558, 514/561, 578; 530/300, 345; 554/103, 114; 562/11, 16, 104, 574

(56) References Cited

U.S. PATENT DOCUMENTS

| | | | | |
|---|---|---|---|---|
| 3,530,162 A | * | 9/1970 | Fuchs ........................ | 558/303 |
| 4,015,008 A | * | 3/1977 | Barer et al. ................. | 514/423 |
| 4,045,578 A | * | 8/1977 | Kaminski et al. ........... | 514/550 |
| 6,153,650 A | * | 11/2000 | Bryans et al. .............. | 514/561 |

FOREIGN PATENT DOCUMENTS

| | | |
|---|---|---|
| CA | 2200795 | 3/1997 |
| GB | 2072371 | * 9/1981 |

OTHER PUBLICATIONS

Martincigh et al. Antioxidant Chemistry: Hypotaurine–Taurine Oxidation by Chlorite. J. Phys. Chem. 1998, vol. 102, pp. 9838–9846.*

Thomas et al. Myeloperoxidase–Catalyzed Incorporation . . . Biochemistry. vol. 21, pp. 6299–6308, 1982.*

Chemical Abstract 129: 49373v, Aug. 3, 1998.*

Hawkins, C.L. et al., "Reaction of HOCl with amino acids and peptides: EPR evidence for rapid rearrangement and fragmentation reactions of nitrogen–centred radicals." *J. Chem. Soc., Perkins Trans.* 2:1937–1945 (1998).

Grisham, M.B. et al., "Role of monochloramine in the oxidation of erythrocyte hemoglobin by stimulated neutrophils" *J. Biol. Chem.* 259:6766–6772 (1984).

Grisham, M.B. et al., "Chlorination of endogenous amines by isolated neutrophils" *J. Biol. Chem.* 259:10404–10413 (1984).

Thomas, E.L., "Myeloperoxidase, hydrogen peroxide, chloride antimicrobial system: nitrogen–chlorine derivatives of bacterial components in bactericidal action against *Escherichia coli*" *Infection and Immunity* 24:522–531 (1979).

Thomas, E.L., "Myeloperoxidase–hydrogen peroxide–chloride antimicrobial system: effect of exogenous amines on antibacterial action against *Escherichia coli*" *Infection and Immunity* 25:110–116 (1979).

Thomas, E.L. et al., "Myeloperoxidase–dependent effect of amines on functions of isolated neutrophils" *J. Clin Invest.* 72:441–454 (1983).

Vit, J., et al., "New derivatives of amino acids N,N–dichloroglycine and N,N–dichloro–B–alanine" *Synthetic Communications* 6:1–4 (1976).

Weiss, S.J. et al., "Chlorination of taurine by human neutrophils" *J. Clin Invest.* 70:598–607 (1982).

* cited by examiner

*Primary Examiner*—Jeffrey E. Russel
(74) *Attorney, Agent, or Firm*—Stephen J. Scribner; Carol Miernicki Steeg

(57) ABSTRACT

A method of treating a CNS disorder in a subject in need of such treatment, the method comprising administering to the subject an effective amount of an N'N'-dichlorinated amino acid, peptide, peptidomimetic, amine, or a pharmacologically acceptable analogue or derivative thereof, such that a CNS disorder is treated. An N'N'-dichlorinated amino acid, peptide, peptidomimetic, or amine capable of crossing the blood-brain barrier of a subject when administered thereto.

40 Claims, No Drawings

N'N'-DICHLORINATED OMEGA-AMINO ACIDS AND USES THEREOF

RELATED APPLICATION

This application claims the benefit of the filing date of U.S. Provisional Patent Application No. 60/156,528, filed Sep. 29, 1999, the contents of which are incorporated herein by reference in their entirety.

FIELD OF THE INVENTION

This invention relates to methods of modifying amino acids, small peptides, or other primary amines, so that they are able to cross the blood-brain barrier and reach the central nervous system, and products of such methods. In particular, this invention relates to dichlorination of omega-amino acids such as taurine, homotaurine, and GABA, to allow them to cross the blood-brain barrier and reach the central nervous system.

BACKGROUND OF THE INVENTION

The ω-amino acids are a group of substances consisting of a terminal unsubstituted amino group and an acidic (phosphonic, sulphonic, sulphinic or carboxyl) group separated by an aliphatic (unbranched) carbon chain $(NH_2(CH_2)_nSO_3H_2, -PO_3H, SO_2H_2,$ or $NH_2(CH_2)_nCOOH; n=1-5)$. Some of these amino acids are formed in vivo from the enzymic α-decarboxylation of the corresponding α-amino-α-carboxyl amino acid: glutamate/γ-aminobutyric acid (GABA), cysteic acid/taurine, homocysteic acid/homotaurine. Although evidence for the existence in tissues of a number of such decarboxylases is quite convincing (Abbott et al., 1981; Almarghini et al., 1991; Huxtable and Lippincott, 1982; Irving et al., 1986), the in vivo synthesis of taurine nevertheless appears marginal despite its presence in μmolar concentrations in many organs, notably brain, heart and skeletal muscle (Guilarte, 1989; van Gelder and Bélanger, 1988), while homotaurine may only exist as traces in the body. In human and several other mammalian species, especially carnivores, taurine appears mostly to derive from nutrition; in herbivores it originates from synthesis by enteric bacteria, while the origin of the very high concentrations of taurine in invertebrate tissues and body fluids is not yet entirely clear. In contrast, neural tissue, especially, is rich in glutamic acid decarboxylase and several isoforms have been identified, with different affinities for their co-factors such as pyridoxal phosphate (vitamin $B_6$) (Martin and Rimvall, 1993). Practically all GABA present in neural tissue can be accounted for by α-decarboxylation of glutamic acid which, in turn, originates entirely from in situ synthesis within the CNS. Finally, L-leucine, an α-amino acid, belongs to the group of amino acids which need to be supplied by the diet, and thus is classified as an (nutritionally) essential amino acid.

Both taurine and GABA have been demonstrated in the past 30 years to be essential for normal functioning of the central nervous system (CNS). GABA is now known to represent the principal inhibitory transsynaptic messenger substance in the CNS (Elliott and Florey, 1956; Kravitz et al., 1962). Many CNS dysfunctions marked by excessive synchronized neuronal discharge can be traced back to either an imbalance between the excitatory action of glutamic acid mediated transmitter function and the inhibitory effect of GABA, or to a direct failure in GABAergic inhibition, or to both conditions simultaneously. Because of the intimate precursor-product relationship between glutamic acid and GABA, failure in one transmitter system will eventually always cause secondary modification of the other (Hamberger and van Gelder, 1993). Important disorders of brain function in which an aberration of the glutamate-GABA balance is implicated include, among others, most forms of epilepsy, intractable pain disorders and Huntington's Disease.

As opposed to the glutamate-GABA system which at any one moment directly determines the excitation-inhibition balance in a particular brain region, taurine appears to exert a more tonic influence on the operations of the CNS. By a continuous redistribution of taurine between the intracellular and extracelluar spaces via a series of uptake and release mechanisms, as well as by ongoing readjustment of the amount of taurine free in the cytoplasm and that sequestered (i.e., bound) in some form within the cell, taurine controls or prevents excessive fluctuations in the volume of the cerebral spinal fluid (CSF) and of the water content within neural tissue (van Gelder, 1989; van Gelder, 1990). Changes in the dimensions of the intercellular spaces, as well as in the volumes of neurons and apposing glial cells, are a consequence of water redistribution which occurs proportionally to neural tissue discharge rates and the accompanying changing rates of energy metabolism: glucose to ATP, $CO_2$ and water. Taurine thus functions as the principal osmol to counteract such volume changes, a role probably related to its very slow or, indeed, absence of metabolic transformation. Either in addition to this osmotic role of taurine in the CNS and, probably, other organ tissues such as heart and skeletal muscle, or as a consequence of this function, taurine exerts a strong regulation on the intracellular ratio of free to sequestered calcium. The amount of calcium as the free ion in the cytoplasm of a neuron is a key determinant of neuronal excitability and discharge patterns.

Ratios of taurine/glutamate neural tissue contents and blood concentrations are remarkably stable in various species and changes in these ratios are often found in association with a number of severe disorders such as epilepsy, infant malnutrition, and cerebral trauma (Armstrong, 1973; Chesney, 1988; Räihä et al., 1976; van Gelder, 1972). Furthermore, in such circumstances absolute taurine levels are often found decreased, which, in light of the very constant and species characteristic organ content of taurine normally observed, suggests an important malfunction of a major homeostatic mechanism.

SUMMARY OF THE INVENTION

In accordance with a broad aspect of the invention there is provided a method of treating a CNS disorder in a subject in need of such treatment, the method comprising administering to the subject an effective amount of an N'N'-dichlorinated amino acid, peptide, peptidomimetic, amine, or a pharmacologically acceptable analogue or derivative thereof, such that a CNS disorder is treated. The method may include administering to the subject an effective amount of an N'N'-dichlorinated amino acid, or a pharmacologically acceptable analogue or derivative thereof, of the general formula I:

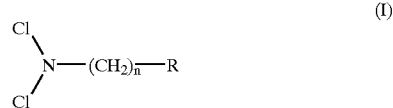

(I)

wherein R is a phosphonic, sulphonic, or carboxyl group, and n is an integer selected such that the biodistribution of the compound for an intended target site is not prevented while maintaining the activity of the compound. According to the method of the invention, n may be an integer from 1 to 10; preferably, n may be an integer from 1 to 5. In certain embodiments, the invention provides a peptide wherein a compound of formula I is the N-terminal residue. In a preferred embodiment of the invention, the amino acid is ω-amino acid selected from the group consisting of taurine, homotaurine, γ-aminobutyric acid, β-alanine, and analogues and derivatives thereof.

The method of the invention may be used to treat a CNS disorder characterized by an abnormality in the profile of one or more amino acids or associated with excessive synchronized neuronal discharge. In various embodiments, the method of the invention may be used to treat an abnormality which is an imbalance in the ratio of taurine and glutamate, or a CNS disorder characterized by an imbalance between the excitatory activity associated with glutamic acid and the inhibitory activity associated with GABA, by a direct failure in GABAergic inhibition, or by both. The method of the invention may be used to treat such CNS disorders as epilepsy, intractable pain disorders, Huntington's Disease, Parkinson's Disease, and abnormalities associated with CNS trauma. The method of the invention may also be used to treat a tumour or a CNS disorder associated with infant malnutrition.

By another broad aspect of the invention, there is provided an N'N'-dichlorinated amino acid, peptide, peptidomimetic, or amine capable of crossing the blood-brain barrier of a subject when administered thereto. The invention may provide an N'N'-dichlorinated amino acid, peptide, peptidomimetic, having a molecular weight (MW) in the range of about 50 to about 4,000 Da, or an N'N'-dichlorinated peptide comprising from 1 to about 20 amino acids.

In a preferred embodiment, the invention provides an N'N'-dichlorinated amino acid of the general formula I:

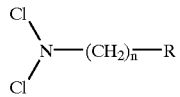

(I)

wherein R is a phosphonic, sulphonic, or carboxyl group, and n is an integer selected such that the biodistribution of the compound for an intended target site is not prevented while maintaining the activity of the compound; and wherein n is an integer greater than 2 when R is a carboxyl group, or a pharmacologically acceptable analogue or derivative thereof. According to various embodiments, the invention provides an N'N'-dichlorinated amino acid of general formula (I) wherein n is an integer from 2 to 10 when R is a phosphonic or sulphonic group, and wherein n is an integer from 3 to 10 when R is a carboxyl group. According to other embodiments, the invention provides an N'N'-dichlorinated amino acid of general formula (I) wherein n is an integer from 2 to 5 when R is a phosphonic or sulphonic group, and n is an integer from 3 to 5 when R is a carboxyl group.

In a preferred embodiment, the invention provides an N'N'-dichlorinated ω-amino acid selected from the group consisting of taurine, homotaurine, γ-aminobutyric acid, and analogues and derivatives thereof.

By yet another aspect of the invention there is provided a pharmaceutical composition comprising an N'N'-dichlorinated amino acid, peptide, peptidomimetic, or amine, and a pharmacologically acceptable vehicle therefor, wherein the N'N'-dichlorinated amino acid, peptide, peptidomimetic, or amine is capable of crossing the blood-brain barrier of a subject when administered thereto. A pharmaceutical composition according to the invention may comprise an N'N'-dichlorinated amino acid, wherein said amino acid or pharmacologically acceptable analogue or derivative thereof is of the general formula I:

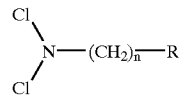

(I)

wherein R is a phosphonic, sulphonic, or carboxyl group, and n is an integer selected such that the biodistribution of the compound for an intended target site is not prevented while maintaining the activity of the compound. In various embodiments, n may be an integer from 2 to 10, and preferably, from 2 to 5.

In a preferred embodiment, the invention provides a pharmaceutical composition comprising an N'N'-dichlorinated ω-amino acid selected from the group consisting of taurine, homotaurine, γ-aminobutyric acid, β-alanine, and analogues and derivatives thereof, and a pharmacologically acceptable vehicle therefor.

Pharmacological compositions according to the invention provide a therapeutically effective amount of the active compound to a subject.

In accordance with another aspect of the invention, there is provided a method of synthesizing a dichlorinated α-amino acid, comprising dichlorinating the α-amino acid in a two-phase system comprising aqueous hypochlorite with an inert immiscible solvent.

In accordance with another aspect of the invention, there is provided a method of synthesizing a dichlorinated amino sulphonate, comprising dichlorinating the amino sulphonate in an aqueous solvent followed by desalting.

DESCRIPTION OF THE INVENTION

Given the importance of the GABA/glutamate and taurine balance in the CNS for normal brain function, many attempts have been made over the past 30 years to increase GABA or taurine levels in neural tissue. However, for both of these naturally occurring ω-amino acids, certain blood-brain barrier (BBB) systems prevent even very high blood concentrations of GABA or taurine from altering the neural tissue content or extracelluar fluid concentrations, including the cerebral spinal fluid (CSF) (Lefauconnier et al., 1978; van Gelder and Elliott, 1958). The use of BBB permeable enzyme inhibitors of GABA aminotransferase (the enzyme which metabolizes GABA) can circumvent the presence of these barriers. Another metabolic approach has been to synthesize analogues of GABA which cross the BBB and prevent re-uptake of GABA once released from its inhibitory nerve terminal at the synapse. Both types of agents are now either in use or in clinical trial for use in the management of seizure disorders, ethanol withdrawal symptoms and intractable pain disorders (Bialer et al., 1996). With respect to taurine, no compound has been developed so far which can mimic its function in the CNS. As to homotaurine, which like taurine has been demonstrated to possess anti-epileptic properties, provided the developing brain dysfunction is associated with or caused by brain trauma, this compound appears somewhat less effective than taurine itself. Clearly it would be of great clinical interest if compounds were available which could act as BBB permeable precursors of taurine, homotaurine, and GABA, or other amino acids and peptides impermeable to the BBB, to be converted within the CNS to the original (amino acid) product.

In accordance with a broad aspect of the present invention there is provided a method of treating a subject having a CNS disorder, the method involving administering to the subject compounds capable of crossing the BBB, and which are converted in the CNS to amino acids and amino acid products. In effect, compounds employed in the invention are prodrugs for such amino acids and amino acid products. In accordance with the invention, compounds are administered in a therapeutically effective amount and usually with a pharmaceutically acceptable vehicle.

As used herein, the term "therapeutically effective amount" means an amount of the compound sufficient to prevent, reduce, manage, or ameliorate undesirable CNS disorders, as determined using assays of conventional design, in an inflicted subject without causing adverse effects.

As used herein, the term "pharmaceutically acceptable" means acceptable for use in the pharmaceutical and veterinary arts; e.g., non-toxic and not adversely affecting the activity and bioavailability of the compound.

The methods of the invention comprise administering to the subject an effective amount of an N-chlorinated amino acid, small peptide (e.g., peptide having a molecular weight (MW) in the range of about 50 to about 4,000 Da, or 1 to about 20 amino acids), peptidomimetic, or primary amine. CNS disorders treatable with methods of the present invention include, but are not limited to, conditions characterized by or associated with synchronized neuronal discharge and tumours. Examples of CNS conditions potentially giving rise to or associated with synchronized neuronal discharge that are treatable with the invention include epilepsy, intractable pain disorders, Huntington's Disease, Parkinson's Disease, and abnormalities associated with CNS trauma (e.g., stroke, spinal cord injury, impact trauma). CNS disorders associated with synchronous neuronal discharge also result from infant malnutrition. Tumours treatable with the invention include, for example, those characterized by glial abnormalities, and include oligodendrocytomas, astrocytomas and neuroblastomas. Yet other tumours treatable with the invention are those characterized by a specific peptide abnormality or an amino acid imbalance, for example taurine abnormality, wherein a tumour exhibits elevated taurine uptake.

According to a preferred embodiment of the invention, the method comprises administering to a subject an N'N'-dichlorinated amino acid of the general formula I:

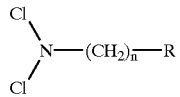
(I)

wherein R is a phosphonic, sulphonic, or carboxyl group, and n is an integer selected such that the biodistribution of the compound for an intended target site is not prevented while maintaining the activity of the compound. Preferably, n=1 to 10, and more preferably n=1 to 5. In a more preferred embodiment of the invention, the compound administered is an N'N'-dichlorinated ω-amino acid. Examples of N'N'-dichlorinated ω-amino acids suitable for administering in accordance to the methods of the invention are dichlorotaurine, dichlorohomotaurine, dichloro-β-alanine, and dichloro-γ-aminobutyric acid, and analogues and derivatives thereof. Analogues and derivatives have the same or substantially the same activity as the above-described N-chlorinated compounds and include, for example, salts, esters and peptides containing one or more of these compounds.

As used herein, the term "peptidomimetic" is intended to include peptide analogues which serve as appropriate substitutes for peptides in interactions with, for example, receptors and enzymes. The peptidomimetic must possess not only affinity, but also efficacy and substrate function. That is, a peptidomimetic exhibits functions of a peptide, without restriction of structure to amino acid constituents. Peptidomimetics, methods for their preparation and use are described in Morgan et al. (1989), the contents of which are incorporated herein by reference.

As used herein, the term "N-chlorinated" encompasses mono- and dichlorinated compounds.

As used herein, the term "treating a CNS disorder" encompasses treatment, prevention, and amelioration of such a disorder, including inhibiting the progression of the disorder, as well as managing the symptoms, e.g., reducing a symptom such as pain. In addition, the term "treating a CNS disorder" as contemplated in this application, means improving a physiological state of a subject, which state is associated with a CNS disorder, though that individual may or may not have been diagnosed with a said disorder.

In accordance with another aspect of the present invention there is provided an N-chlorinated compound capable of crossing the BBB, which is converted in the CNS to an amino acid or amino acid product. Specifically, N-chlorinated compounds of the invention include amino acids, small peptides (e.g., peptides having a molecular weight (MW) in the range of about 50 to about 4,000 Da, or 1 to about 20 amino acids), peptidomimetics, and other primary amines.

In a preferred embodiment of the invention, the compound is an N'N'-dichlorinated amino acid of the general formula I:

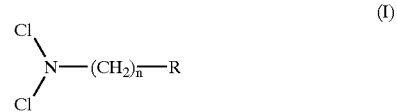
(I)

wherein R is a phosphonic, sulphonic, or carboxyl group, and n is an integer selected such that the biodistribution of the compound for an intended target site is not prevented while maintaining the activity of the compound. Preferably, n=2 to 10, and more preferably n=2 to 5. In a more preferred embodiment of the invention, the compound is an N'N'-dichlorinated ω-amino acid. Examples of N'N'-dichlorinated ω-amino acids of the invention are dichlorotaurine, dichlorohomotaurine, dichloro-β-alanine, and dichloro-γ-aminobutyric acid, and analogues and derivatives thereof. Analogues and derivatives include, for example, salts, esters and peptides containing one or more of these compounds.

In accordance with a another aspect of the invention there is provided a pharmaceutical composition comprising an N-chlorinated compound and a pharmacologically acceptable vehicle therefor, wherein the N-chlorinated compound is capable of crossing the blood-brain barrier of a subject when administered thereto. A pharmaceutical composition according to the invention may comprise an N-chlorinated compound such as an amino acid, small peptide (e.g., peptide having a molecular weight (MW) in the range of about 50 to about 4,000 Da, or 1 to about 20 amino acids), peptidomimetic, and primary amine. An N-chlorinated compound of the pharmaceutical composition of the invention is converted in the CNS to an amino acid or amino acid product. A pharmaceutical composition according to the invention may comprise an N'N'-dichlorinated amino acid, wherein said amino acid or pharmacologically acceptable analogue or derivative thereof is of the general formula I:

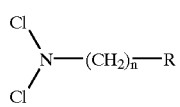

wherein R is a phosphonic, sulphonic, or carboxyl group, and n is an integer selected such that the biodistribution of the compound for an intended target site is not prevented while maintaining the activity of the compound. In various embodiments, n may be an integer from 2 to 10, and preferably, from 2 to 5.

In a preferred embodiment, the invention provides a pharmaceutical composition comprising an N'N'-dichlorinated ω-amino acid selected from the group consisting of taurine, homotaurine, γ-aminobutyric acid, β-alanine, and analogues and derivatives thereof.

According to the invention, upon administration to a subject, N'N'-dichlorinated amino acids, peptides, primary amines are converted in the CNS to their unchlorinated forms. Thus, for example, the N'N'-dichlorinated ω-amino acids mentioned above are converted in the CNS to taurine, homotaurine, β-alanine, and GABA, respectively. The invention is useful in treating abnormalities in amino acid profiles of the CNS. In particular, the compounds of the preferred embodiments of the invention are useful for treating abnormalities associated with an imbalance in the ratio of taurine/glutamate in neural tissues. Examples of such abnormalities are those associated with disorders such as epilepsy, infant malnutrition, intractable pain disorders, Huntington's Disease, and Parkinson's Disease, as well as abnormalities associated with CNS trauma, as described above.

The present invention also provides methods for the preparation of N-chlorinated amino acids and small peptides, peptidomimetics, or other primary amines. N-chlorination of these amino acids, peptides, and amines allows them to cross the BBB. According to preferred embodiments of the invention, there are provided methods for the preparation of N'N'-dichlorinated ω-amino acids dichlorotaurine, dichlorohomotaurine, dichloro-β-alanine, and dichloro-γ-aminobutyric acid, as well as N'N'-dichloro-L-leucine.

Heretofore, there have been some reports on N-chlorination of amino acids and other primary amines, though the reaction products are generally known to be quite unstable (Abia et al., 1998; Grisham et al., 1984; Thomas, 1979; Weiss et al., 1982). N-chlorotaurine has been shown to form as part of the mechanism of phagocytosis by neutrophilic leukocytes (Thomas, 1979; Weiss et al., 1982). Studies on this mechanism indicate that this taurine product exists transiently in vivo but, in the absence of the neutrophils, N-monochlorotaurine appears fairly stable in an aqueous environment; toxicity appears to be low until reacted with $NH_4^+$ to yield the oxidizing agent monochloroamine ($NH_2Cl$). Moreover, both those studies suggest that chlorinated amines will be far more lipophilic than their corresponding precursor (Abia et al., 1998). This is in accord with the present invention; all other physico-chemical properties being equal, lipophilic compounds tend to cross the blood-brain barrier systems with greater ease than those that are strictly water soluble. Additionally, chlorination of primary amines has been shown to occur readily in the presence of a source for hypochlorite ion, with proof of (transient) chlorinated product formation demonstrated by UV absorbance, thin layer chromatography, and oxidation of 5-thio-2-nitrobenzoic acid (Thomas, 1979; Weiss et al., 1982). Finally, it should be noted that N-chlorination of the amino acids β-alanine and glycine has been carried out, but these chlorinated forms were reported to be extremely unstable and their synthesis was cumbersome (Vit and Barer, 1976).

The compounds and compositions of the invention are administered to subjects in a biologically compatible form suitable for administration in vivo. By "biologically compatible form suitable for administration in vivo" is meant a form of an N-chlorinated amino acid, peptide, peptidomimetic, amine, or derivative, analogue, or metabolite thereof to be administered in which any toxic effects are outweighed by the preventative therapeutic effects. The therapeutic compounds of the invention can be administered in a pharmaceutically acceptable vehicle. As used herein "pharmaceutically acceptable vehicle" includes any and all solvents, excipients, dispersion media, coatings, antibacterial and antifungal agents, isotonic and absorption delaying agents, and the like which are compatible with the activity of the compound and are physiologically acceptable to the subject. An example of the pharmaceutically acceptable vehicle is buffered normal saline (0.15 M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

As used herein, the term "subject" is intended to include living organisms in which a response can be elicited, e.g., mammals. Examples of subjects include humans, dogs, cats, mice, rats, and transgenic species thereof. As would be apparent to a person of skill in the art, the animal subjects employed in the working examples set forth below are reasonable models for human subjects with respect to the tissues and biochemical pathways in question, and consequently the methods, therapeutic compounds and pharmaceutical compositions directed to same. As evidenced by Mordenti (1986) and similar articles, dosage forms for animals such as, for example, rats can be and are widely used directly to establish dosage levels in therapeutic applications in higher mammals, including humans.

Administration of an effective amount of the compositions of the present invention is defined as an amount effective, at dosages and for periods of time necessary to achieve the desired result. For example, an effective amount of an N-chlorinated amino acid, peptide, or amine according to the invention may vary according to factors such as the age, sex, weight, and disease state of the individual, and the ability of the N-chlorinated amino acid, peptide, or amine to elicit a desired response in the individual. Dosage regimens may be adjusted to provide the optimum response. For example, several divided doses may be administered daily or the dose may be proportionally reduced as indicated by the exigencies of the therapeutic situation.

The active compound (e.g., an N-chlorinated amino acid, peptide, or amine) may be administered in a convenient manner such as by oral administration, transdermal application, rectal administration, or by subcutaneous, intraocular, intravenous, intramuscular or intraperitoneal administration, and the like (e.g., by injection). Depending on the route of administration, the active compound may be coated in a material to protect the compound from the action of enzymes, acids and other natural conditions which may inactivate the compound. For oral administration the compounds may be provided in the form of, for example, a powder, pill, or a liquid, and in any such form the compounds would be combined with suitable carriers, solubilizers, stabilizers, coloring agents, and the like, as required, as is well known in the art.

To administer a therapeutic compound of the invention by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

Therapeutic compounds of the invention may also be administered parenterally (e.g., intramuscularly, intravenously, intraperitoneally, intraspinally, or intracerebrally). Dispersions can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of neurological conditions in subjects.

Therapeutic compositions can be administered in time-release or depot form, to obtain sustained release of the therapeutic compounds over time. The therapeutic compounds of the invention can also be administered transdermally (e.g., by providing the therapeutic compound, with a suitable carrier, in patch form).

Administration of the more reactive forms of the inventive compounds, such as certain N-chlorinated amino acids, may be facilitated if they are provided in prodrug form. According to the invention, a subject may be administered a prodrug which is converted in vivo to a compound of the invention that can cross the BBB (See Silverman, 1992). Prodrugs (for example, an ester which is hydrolyzed in vivo) are employed in the art to alter biodistribution of an active compound or to modify metabolic or kinetic properties thereof.

It will be appreciated that the ability of a compound of the invention to mitigate CNS disorders will, in certain embodiments, be evaluated by observation of one or more symptoms or signs associated with CNS disorders in vivo. Thus, for example, the ability of a compound to mitigate CNS disorders may be associated with an observable improvement in a clinical manifestation of the underlying CNS disorder-related disease state or condition, or a slowing or delay in progression of symptoms of the disorder. Thus, monitoring of clinical manifestations of a disorder can be useful in evaluating the CNS disorder-mitigating efficacy of a compound of the invention.

The contents of all scientific publications cited in this application are incorporated herein by reference.

Synthesis, quantitative isolation and characterization by NMR and mass spectroscopy of N'N'-dichlorinated amino acids according to preferred embodiments of the invention, as well as biological testing, are described in the Working Examples below. Synthesis of N'N'-dichloro-L-leucine, whose precursor is classified as nutritionally essential for mammals, is included as a reference compound to distinguish between biological effects caused by $NH_2Cl$ production upon in vivo dechlorination, and those caused by reformation of the free, neuroactive amine. The below Examples are not intended to be limiting in any respect.

WORK EXAMPLES

Example 1

Synthesis of N'N'-dichlorotaurine

Taurine (1.5 g) was suspended in a mixture of methanol (50 mL) and 4 M aqueous hydrochloric acid (25 mL). To this was added in small aliquots 4–6% aqueous sodium hypochlorite (40 mL) with stirring. The taurine dissolved with evolution of gentle heat. After 2 h the solution was concentrated (below 30° C.) to a small volume. Ethanol (200 mL) was added and the precipitated sodium chloride was removed by filtration. This procedure was repeated until no more precipitate formed. After concentration to a small volume of oily residue, 50/50 methanol-ethyl acetate (100 mL) was added, and the mixture was again filtered to remove residual sodium chloride. Upon reconcentration, the residue was treated with 0.04 M aqueous hydrochloric acid in acetone (25 mL). Slow concentration yielded white, iridescent plates, (0.7 g). The product showed as a single spot on TLC (Merck $SiO_2$) Rf 0.70 (32/1/1 acetonitrile/acetic acid/water). Detection was by spraying with 2% KI-starch (yellow-brown) followed by ethanolic ninhydrin (faintly pink); M.P. 148° C. UV ($\lambda_{max}$) 310 nm ($\epsilon 1.851 \times 10^2$, 95% ethanol); $^1$Hmr ($D_2O$) 3.05–3.2(2H, m) and 3.95–4.05 (2H, m); MS (es–): 191.9(18.76%), 193.8 (13.41%), 195.8 (2.83%). The compound is reasonably stable for up to a month at –10° C. when dry; it is stable in water for at least 3 h at ambient temperature, based on TLC and NMR monitoring; little or no decomposition occurred over 48 h in 95% ethanol.

Example 2

Synthesis of N,N-dichlorohomotaurine

The chlorinaton and desalting methodology was essentially similar to that for taurine. Dichlorohomotaurine is more unstable than its taurine homologue in a humid atmosphere and is more soluble in nonpolar solvents. Final isolation was from 50/50 ('/,) diethylether-methanol plus dichloromethane, followed by slow evaporation at approximately 0–4° C. M.P. 197° C.; UV: $\lambda_{max}$ 308 ($\epsilon 1.486 \times 10^2$, 95% ethanol); $^1$Hmr ($D_2O$) δ: 2.05–2.15 (2H, m, $\alpha CH_2$), 2.95–3.05 (2H, m, $\beta CH_2$), 3.9–4.0 (2H, m, $\gamma CH_2$); MS (es–): 205.9(1.4%), 207.9(0.88%), 210.0(0.31%). Fairly hygroscopic and readily decomposed to homotaurine ($t_{1/2}$24 h) in water.

Example 3

Synthesis of N,N-dichloro-γ-aminobutyric Acid and N'N'-dichloro-β-alanine

GABA or β-alanine (1.5 g) was dissolved in 4M hydrochloric acid (10 mL), to which was added dichloromethane (250 mL). Sodium hypochlorite (50 mL) in small aliquots was added with vigorous agitation over a period of 2 h. The dichloromethane layer was washed consecutively with 5 mL, 10 mL and 5 mL aliquots of saturated brine then dried with sodium sulfate. The filtered solution was concentrated at <0° C. to leave a viscous pale-yellow oil. Dichloromethane (25 mL) was again added, the solution was filtered once more to remove any remaining precipitate, and then reconcentrated and dried under high vacuum. The product was stored under nitrogen at –10° C. Thin layer chromatography demonstrated a single spot at Rf 0.80+ which strongly reacted to KI-starch and faintly to ninhydrin.

N,N-dichloro-GABA: UV: $\lambda_{max}$ 308 nm ($\epsilon 2.974 \times 10^2$, 95% ethanol); $^1$Hmr ($CDCl_3$) δ: 1.95–2.05 (2H, m,$\alpha CH_2$), 2.4–2.5 (2H, m, $\beta CH_2$), 3.6–3.75 (2H, m, $\gamma CH_2$). Decomposition in water was about 50% in 3 h at room temperature (TLC monitored).

N,N-dichloro-β-alanine: UV: $\lambda_{max}$ 318 nm ($\epsilon 2.332 \times 10^2$, 95% ethanol); $^1$Hmr ($CDCl_3$) δ: 1.85–1.95 (2H, m, $\alpha CH_2$), 3.85–3.95 (2H, m, $\beta CH_2$). More stable than N,N-dichloro-GABA in water or 95% ethanol.

Example 4

Synthesis of N,N-dichloro-L-leucine

The procedure for the synthesis of N'N'-dichloro-leucine was identical to that for the dichloroGABA. The product is a pale-yellow oil. When stored in dichloromethane, at –10° C.; the compound readily decomposed with an approximate half-life of 1 h. The product demonstrated a Rf 0.44 (32/1 acetonitrile/acetic acid); UV: $\lambda_{max}$ 298 nm ($\epsilon 5.599 \times 10^2$, 95% ethanol) (calculated on an approximated rate of decomposition); $^1$Hmr ($CD_3OD$) δ: 4.08–4.18 (1H, m, $\alpha CH$), 1.7–1.8 (3H, m, $\beta CH_2$ and $\gamma CH$), 0.9–1.0 (6H, m, $CH_3$).

From the above Examples it is apparent that dichlorination of ω-amino acids yields products which vary considerably in their stability. The N'N'-dichloro product of taurine chlorination is stable for at least one month without appreciable decomposition when stored in a nitrogen atmosphere at room temperature, and probably several months more. The most important precaution required for stable storage is the removal of all traces of water. All four compounds show hygric properties, with dichlorotaurine the most and dichloro-GABA and dichloro-leucine being the least stable when in contact with water. A yield of between 30–60% was obtained, which can be improved by more efficiently exploiting the fact that primary amines are far less soluble than their chlorinated products in non-polar solvents. Those of ordinary skill in the art will recognize that the methods for isolation of the chlorinated amino acids described here can be extended to other α-carboxyl amino acids, as well as peptides and proteins.

It should be noted that N'N'-dichlorinated carboxyl amino acids according to the invention are preferably prepared using the above-described two-phase synthesis, while N'N'-dichlorinated phosphonated and sulphonated amino acids according to the invention are preferably prepared using the aqueous solvent and desalting. Taurine and homotaurine are not made using the two-phase system because they are too polar.

The extraction/isolation methods described above provide compounds of the invention in a substantially purified form. The inventors have found for certain compounds of the invention that extraction with a solvent including methanol is highly preferred. Preferred methods of purification generally include extractions with a mixture of methanol and another less polar organic solvent such as ethyl acetate or dichloromethane, generally in approximately equal parts. Equivalent methods of extraction/purification as could be developed by a person skilled in the art without undue experimentation are also encompassed by the invention.

Example 5

Biological Testing

Ten male mice (20 g) were injected i.p. (200 mg/Kg) with dichlorotaurine (0.2 mL of a 20 mg/mL 0.9% NaCl (5 mice)

or water (5 mice). Within 5 min all animals demonstrated severe ataxia, laboured breathing and grooming behaviour towards the site of injection. By 5–7 min each mouse became very quiet, showed strongly reduced responsiveness to environmental stimuli, and reduced mobility. When prodded, profound ataxia remained clearly evident. Ten other mice received taurine (200 mg/Kg) while a third group of ten received 0.2 mL of isotonic saline (0.9% NaCl). None of the taurine or saline injected animals showed any but normal behaviour: vigorous exploration, grooming, nor other signs of any abnormality. Injection schedules were adjusted in such manner that all mice could be killed by cervical dislocation after one hour; the brains including brainstem were removed within 2 min and frozen in liquid nitrogen; spinal cord dissection took approximately 5 min more. All tissues were stored at −70° C.

Two other mice (20 g) received dichlorotaurine (0.1 mL=100 mg/Kg) s.c. at 60 min intervals for three hours. Onset of "sedation" occurred with a similar time course, 5 min following the first injection. The administration of the two subsequent injections did not aggravate nor modify the tranquil behaviour. Two to three hours following the last injection the animals started to return to normal behaviour. Observation for the next 24 h did not reveal any abnormalities.

Finally, two other mice (20 g) received dichlorohomotaurine (0.2 mL; 20 mg/mL=200 mg per Kg) and were killed one hour later to obtain the brain-cerebellum-brainstem and spinal cord. Behaviour following injection was almost indistinguishable from that observed with the taurine homologue.

Example 6

Catecholamine and Indoleamine Determinations

Procedures for dissection of brain regions and tissue sample processing were identical to those described previously (Reader, 1982). The CNS was subdivided into: frontal cortex, caudate-putamen, hippocampus, brainstem, cerebellum and spinal cord. For each of these CNS subdivisions the following monoamines and their metabolites were determined by HPLC (Reader, 1982): dopamine, noradrenaline, 3,4-dihydroxyphenylacetic acid, 5-hydroxyindole-3-acetic acid, serotonin, 5-hydroxy-L-tryptophan, 5-hydroxytryptophol, homovanilic acid, and 3-methoxytyramine.

No differences in the neural tissue content of any of the above monoamines or their metabolites was noted when the dichloroamine injected animals were compared to either the saline or taurine treated control groups.

Example 7

Biological Testing

Three Sprague-Dawley rats were each injected with taurine (200 mg/kg) (control), and another three Sprague-Dawley rats were each administered dichlorotaurine (200 mg/kg): one at 10 min (i.p.), one at 20 min (i.p.) and one at 30 min (i.v.) prior to sacrifice. The animals were anesthetized with ether and then sacrificied by cardiac perfusion with phosphate buffered saline for 5 min, before the brains were removed at room temp.

Brain regions were dissected by hand on a glass cold plate (4–6° C.). The samples were homogenized in 9× weight by volume of water, then perchloric acid was added to a final concentration of 0.6 M to precipitate proteins. Samples (20 μL) were neutralized with 15 μL 2M KHCO$_3$. The extracts were centrifuged and supernatants were diluted with water 1:100. Amino acid analysis was performed by derivatization with o-phthaldialdehyde followed by liquid chromatography (Varian LC 5000 and Schoeffel FS 970 fluorometer). Separation of individual amino acids was achieved with a 5 mm Nuclosil C-18 column (200×4.6 mm) using gradient elution with an increasing concentration of methanol (30–100%) in sodium phosphate buffer (5 mM, pH 5.4). Identification and quantification by peak height was calibrated against a standard amino acid solution.

Data are shown in Table1, below, where each taurine (control) value and dichlorotaurine value is the average of the three respective rats. The amino acid values represent endogenous neural tissue content and not extracellular (release) concentrations. The most pronounced effects of the dichlorotaurine are on the cortex-hippocampus. The data are interpreted as directed towards reduced (↓) excitability. Moreover, the data provide evidence that administration of dichlorotaurine attenuates the pathological consequences of excessive glutamate release, which is known to occur under clinical conditions such as, for example, epilepsy, intractable pain disorders, Huntington's Disease, Parkinson's Disease, and abnormalities associated with CNS trauma (e.g., stroke, spinal cord injury, impact trauma).

TABLE 1

Effect of dichlorotaurine on rat brain amino acid profile.

| | taurine | dichloro-taurine | % change | interpretation |
|---|---|---|---|---|
| | (nmoles/mg wet weight) | | | |
| TAURINE | | | | |
| frontal cortex | 7.67 | 10.00 | +30 | ↓ excitability |
| hippocampus | 7.38 | 11.22 | +52 | |
| brain stem | 2.29 | 2.63 | —* | |
| cerebellum | 5.38 | 5.36 | — | |
| GLUTAMATE | | | | |
| frontal cortex | 15.04 | 11.90 | −20 | ↓ excitability |
| hippocampus | 13.82 | 15.76 | — | |
| brain stem | 8.20 | 7.19 | — | |
| cerebellum | 11.32 | 10.29 | — | |
| GABA | | | | |
| frontal cortex | 2.28 | 2.93 | +29 | ↓ excitability |
| hippocampus | 2.83 | 3.73 | +32 | |
| brain stem | 2.25 | 2.32 | — | |
| cerebellum | 2.25 | 1.97 | — | |
| RATIO GLU/TAU** | | | | |
| frontal cortex | 1.98 | 1.32 | −33 | ↓ excitability |
| hippocampus | 1.91 | 1.45 | −24 | |
| brain stem | 3.73 | 2.50 | −33 | |
| cerebellum | 2.15 | 2.01 | — | |
| RATIO GLY/GLU** | | | | |
| frontal cortex | 0.28 | 0.40 | +42 | ↓ excitability |
| hippocampus | 0.36 | 0.43 | +20 | |
| brain stem | 1.30 | 1.55 | +19 | |
| cerebellum | 0.48 | 0.46 | — | |

*±15% considered non-significant: no change;
**GLY/GLU and GLU/TAU values after 30 min i.v. taurine were the same as for dichlorotaurine, suggesting that i.v. taurine does affect brain amino acids and, therefore also reduces hyperexcitability (Hamberger et al., 1993). Intraperitoneal taurine seems much less effective than i.p. dichlorotaurine.

These Examples show a clear and striking change of behaviour when the chlorinated products are injected either intraperitoneally or subcutaneously in mice. The onset of symptoms is rapid and highly indicative of CNS involvement: ataxia, severe lethargy and tranquilization, diminished reaction to tail pinching (pain). Such observations imply that primary amines, which are implicated in controlling brain excitability and cerebral micro- or macroanatomy, can cross the blood-brain barrier systems in their N-chlorinated form, to be easily reconverted by non-enzymic processes to their naturally occurring form within the CNS. At the relatively high doses used, no apparent toxicity was noted and the symptoms were readily reversible over time. Moreover, while one might postulate that the reduction of the chloroamine might give rise to free radical generation, the unchanging neural tissue contents of dopamine, serotonin and noradrenalin in this respect is very reassuring. These transmitter substances are very susceptible to free radical attack and their levels are rapidly altered following conditions in the CNS that give rise to increased free radical production, such as brain and spinal cord injury. Hence, chemical modification by N-chlorination provides a convenient and practical approach to obtaining analogues of compounds that under normal biological conditions are impermeable to the blood-brain barrier systems but are of great importance for normal brain function.

Those skilled in the art will recognize, or be able to ascertain using no more than routine experimentation, numerous equivalents to the specific procedures and compounds described herein. Such equivalents are considered to be within the scope of this invention and are covered by the claims.

REFERENCES

Abbott R J, Keidan J, Pye J. Nahorski S R (1981): Effect of freezing on gamma-aminobutyric acid levels in human cerebrospinal fluid. J. Neurochem. 37:1042–1044.

Abia L, Armesto X L, Canle M, Garcia M V, Santaballa J A (1998): Oxidation of aliphatic amines by aqueous chlorine. Tetrahedron 54:521–530.

Almarghini K, Remy A, Tappaz M (1991): Immunocytochemistry of the taurine biosynthesis enzyme, cysteine sulfinate decarboxylase, in the cerebellum: Evidence for a glial localization. Neuroscience 43:111–119.

Armstrong M D (1973): Decreased taurine excretion in relation to childbirth, lactation and progestin-estrogen therapy. Clin. Chim. Acta 46:253–256.

Bialer M, Johannessen S I, Kupferberg H J, Levy R H, Loiseau P, Perucca E (1996): Progress report on new antiepileptic drugs: A summary of the Third Eilat Conference. Epil.Res. 25:299–319.

Chesney R W (1988): Taurine: Is it required for infant nutrition. J. Nutrition 118:6–10.

Elliott KAC, Florey E (1956): Factor I-inhibitory factor from brain. J. Neurochem. 1:181–191.

Grisham M B, Jefferson MM, Thomas E L (1984): Role of monochloramine in the oxidation of erythrocyte hemoglobin by stimulated neutrophils. J. Biol. Chem. 259:6766–6772.

Guilarte T R (1989): Regional changes in the concentrations of glutamate, taurine, and GABA in the vitamin B-6 deficient developing rat brain: Association with neonatal seizures. Neurochem. Res. 14:889–897.

Hamberger A, van Gelder N M (1993): Metabolic manipulation of neural tissue to counter the hypersynchronous excitation of migraine and epilepsy. Neurochem. Res. 18:503–509.

Huxtable R J, Lippincott S E (1982): Diet and biosynthesis as sources of taurine in the mouse. J. Nutrition 112:1003–1010.

Irving C S, Marks L, Klein P D, Foster N, Gadde P L, Chase T N, Samuel D (1986): New evidence for taurine biosynthesis in man obtained from $^{18}O_2$ inhalation studies. Life Sci. 38:491–495.

Kravitz E A, Potter D D, van Gelder N M (1962): Gamma-aminobutyric acid distribution in the lobster nervous system: CNS, peripheral nerves and isolated motor and inhibitory axons. Biochem. Biophys. Res. Commun. 7:231–236.

Lefauconnier J-M, Urban F, Mandel P (1978): Taurine transport into the brain in rat. Biochimie (France) 60:381–387.

Martin D L, Rimvall K (1993): Regulation of γ-aminobutyric acid synthesis in brain. J. Neurochem. 60:395–407.

Mordenti (1986): Man versus beast: Pharmacokinetic scaling in mammals. J. Pharm. Sci. 75:1028–1040.

Morgan et al. (1989): Approaches to the discovery of non-peptide ligands for peptide receptors and peptidases. In Ann. Rep. Med. Chem., edited by Virick F J, et al., Academic Press, San Diego, Calif. pp. 243–253.

Räihä N C R, Heinonen K, Rassin D K, Gaull G E (1976): Milk protein quantity and quality in low-birthweight infants: I Metabolic responses and effects on growth. Pediatrics 57:659–674.

Reader T (1982): Catecholamines and serotonin in rat frontal cortex after PCPA and 6-OHDA: Absolute amounts and ratios. Brain Res. Bull. 8:527–534.

Silverman (1982): The Organic Chemistry of Drug Design and Drug Action, Academic Press, Chapter 8.

Strejan et al. (1984): J. Neuroimmunol. 7:27.

Thomas E L (1979): Myeloperoxidase, hydrogen peroxide, chloride antimicrobial system: Nitrogen-chloride derivatives of bacterial components in bactericidal action against *Escherichia coli*. Infection and Immunity 23:522–531.

van Gelder N M (1972): Antagonism by taurine of cobalt—induced epilepsy in cat and mouse. Brain Res. 47:157–165.

van Gelder N M (1989): Brain taurine content as a function of cerebral metabolic rate: Osmotic regulation of glucose derived water production. Neurochem. Res. 14:495–497.

van Gelder N M (1990): Neuronal discharge hypersynchrony and the intracranial water balance in relation to glutamic acid and taurine redistribution: migraine and epilepsy. In: Taurine: Functional Neurochemistry, Physiology, and Cardiology, edited by H Pasantes-Morales et al., Wiley-Liss, Inc, NY. pp. 1–20.

van Gelder N M, Bélanger F (1988): Development of the amino acid pools in chick embryo brain, heart and eye: taurine, valine, glutamine, phosphoethanolamine. J. Neurosci. Res. 19:110–118.

van Gelder N M, Elliott K A C (1958): Disposition of gamma-aminobutyric acid administered to mammals. J. Neurochem. 3:139–143.

Vit J, Barer S J (1976): New derivatives of amino acids N,N-dichloroglycine and N,N-dichloro-β-alanine. Synthetic Communications 6:1–4.

Weiss S J, Klein R, Slivka A, Wei M (1982): Chlorination of taurine by human neutrophils. J. Clinical Investigations 70:598–607.

We claim:

1. A method of treating a CNS disorder in a subject in need of such treatment, the method comprising administering to the subject an effective amount of an N'N'-dichlorinated amino acid, peptide, peptidomimetic, or amine, such that a CNS disorder is treated.

2. The method of claim 1, comprising administering to the subject an effective amount of an N'N'-dichlorinated amino acid of the general formula I:

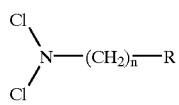
(I)

wherein R is a phosphonic, sulphonic, or carboxyl group, and n is an integer selected such that the biodistribution of the amino acid for an intended target site is not prevented while maintaining the activity of the amino acid.

3. The method of claim 2, wherein n is an integer from 1 to 10.

4. The method of claim 2, wherein n is an integer from 1 to 5.

5. The method of claim 2, wherein said amino acid is an ω-amino acid.

6. The method of claim 5, wherein said ω-amino acid is selected from the group consisting of taurine, homotaurine, γ-aminobutyric acid, and β-alanine.

7. The method of claim 1, wherein said subject is a human being.

8. The method of claim 1, wherein said CNS disorder is characterized by an abnormality in the profile of one or more amino acids or is associated with excessive synchronized neuronal discharge.

9. The method of claim 8, wherein said abnormality is an imbalance in the ratio of taurine and glutamate.

10. The method of claim 9, wherein said CNS disorder is further characterized by an imbalance between the excitatory activity associated with glutamic acid and the inhibitory activity associated with GABA, or by a direct failure in GABAergic inhibition, or by both.

11. The method of claim 10, wherein said CNS disorder is selected from the group consisting of epilepsy, intractable pain disorders, Huntington's Disease, Parkinson's Disease, and abnormalities associated with CNS trauma.

12. A method of treating a CNS disorder in a subject in need of such treatment, the method comprising administering to the subject an effective amount of an N'N'-dichlorinated amino acid, peptide, peptidomimetic, or amine, such that a CNS disorder is treated, wherein said CNS disorder is associated with infant malnutrition.

13. A method of treating a GNS disorder in a subject in need of such treatment, the method comprising administering to the subject an effective amount of an N'N'-dichlorinated amino acid, peptide, peptidomimetic, or amine, such that a CNS disorder is treated, wherein said CNS disorder is a tumour.

14. The method of claim 13, wherein said tumour is characterized by a glial abnormality.

15. The method of claim 13, wherein said tumour is selected from the group consisting of oligodendrocytomas, astrocytomas, and neuroblastomas.

16. An N'N'-dichlorinated amino phosphonic acid capable of crossing the blood-brain barrier of a subject when administered.

17. The N'N'-dichlorinated amino phosphonic acid of claim 16, or a peptide or peptidomimetic comprising said N'N'-dichlorinated amino phosphonic acid, wherein said amino acid, peptide, or peptidomimetic has a molecular weight (MW) up to about 4,000 Da.

18. The N'N'-dichlorinated peptide of claim 17, wherein said peptide comprises from 2 to about 20 amino acids.

19. The N'N'-dichlorinated amino phosphonic acid of claim 16, wherein said amino acid is of the general formula I:

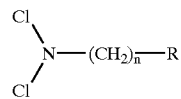
(I)

wherein R is a phosphonic acid group and n is an integer selected such that the biodistribution of the amino acid for an intended target site is not prevented while maintaining the activity of the amino acid.

20. The N'N'-dichlorinated amino phosphonic acid of claim 19, wherein n is an integer from 2 to 10.

21. The N'N'-dichlorinated amino phosphonic acid of claim 19, wherein n is an integer from 2 to 5.

22. A pharmaceutical composition comprising an N'N'-dichlorinated amino phosphonic acid, or a peptide or peptidomimetic comprising an N'N'-dichlorinated amino phosphonic acid, and a pharmacologically acceptable vehicle therefor, wherein said N'N'-dichlorinated amino phosphonic acid, peptide, or peptidomimetic is capable of crossing the blood-brain barrier of a subject when administered thereto.

23. The pharmaceutical composition of claim 22, wherein said amino acid, peptide, or peptidomimetic has a molecular weight (MW) up to about 4,000 Da.

24. A pharmaceutical composition comprising the N'N'-dichlorinated peptide of claim 22, wherein said peptide comprises from 2 to about 20 amino acids.

25. A pharmaceutical composition comprising the N'N'-dichlorinated amino phosphonic acid of claim 22, wherein said amino acid is of the general formula I:

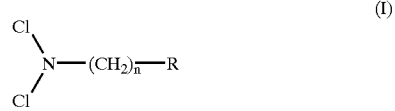
(I)

wherein R is a phosphonic acid group, and n is an integer selected such that the biodistribution of the amino acid for an intended target site is not prevented while maintaining the activity of the amino acid.

26. A pharmaceutical composition comprising the N'N'-dichlorinated amino phosphonic acid of claim 25, wherein n is an integer from 2 to 10.

27. A pharmaceutical composition comprising the N'N'-dichlorinated amino phosphonic acid of claim 25, wherein n is an integer from 2 to 5.

28. A method of synthesizing a dichlorinated amino phosphonic acid or amino sulphonic acid, comprising dichlorinating the amino phosphonic acid or amino sulphonic acid in a two-phase system comprising aqueous hypochlorite with an inert immiscible solvent.

29. A method of synthesizing a dichlorinated amino sulphonate, comprising dichlorinating the amino sulphonate in an aqueous solvent followed by desalting.

30. The method of claim 1, wherein an effective amount of an N'N'-dichlorinated amino acid is administered to a subject, such that a CNS disorder is treated.

31. The method of claim 1, wherein an effective amount of an N'N'-dichlorinated peptide is administered to a subject, such that a CNS disorder is treated.

32. The method of claim 1, wherein an effective amount of an N'N'-dichlorinated peptidomimetic is administered to a subject, such that a CNS disorder is treated.

33. The method of claim 1, wherein an effective amount of an N'N'-dichlorinated amine is administered to a subject, such that a CNS disorder is treated.

34. The method of claim 1, wherein said amino acid is an ω-amino acid.

35. The method of claim 1, wherein said N'N'-dichlorinated amino acid is N'N'-dichlorotaurine.

36. A method of synthesizing a dichlorinated amino phosphonate, comprising dichlorinating the amino phosphonate in an aqueous solvent followed by desalting.

37. The method of claim 28, wherein said dichlorinated amino phosphonic acid or amino sulphonic acid is capable of crossing the blood-brain barrier.

38. The method of claim 29, wherein said dichlorinated amino sulphonate is capable of crossing the blood-brain barrier.

39. The method of claim 36, wherein said dichlorinated amino phosphonate is capable of crossing the blood-brain barrier.

40. The method of claim 1, wherein said CNS disorder is selected from the group consisting of epilepsy, intractable pain disorders, Huntington's Disease, Parkinson's Disease, and abnormalities associated with CNS trauma.

* * * * *

UNITED STATES PATENT AND TRADEMARK OFFICE
CERTIFICATE OF CORRECTION

PATENT NO. : 6,451,761 B1
DATED : September 17, 2002
INVENTOR(S) : Nico M. Van Gelder and Raymond J. Bowers It is certified that error appears in the above-identified patent and that said Letters Patent is hereby corrected as shown below:

Column 1, line 4 through Column 20, line 10,
"N'N'-dichlorinated" should be -- N,N-dichlorinated -- (all occurrences); "N'N'-dichloro-" should be -- N,N-dichloro- -- (all occurrences); and "N'N'-dichlorotaurine" should be -- N,N-dichlorotaurine -- (all occurrences).

Column 17,
Line 45, "GNS" should be -- CNS --;

Signed and Sealed this

Thirteenth Day of January, 2004

JON W. DUDAS
*Acting Director of the United States Patent and Trademark Office*